United States Patent [19]

Chang

[11] Patent Number: 4,547,595

[45] Date of Patent: Oct. 15, 1985

[54] METHOD OF REACTIVATING GROUP VIII ANIONIC HYDROFORMYLATION CATALYSTS

[75] Inventor: Biau-Hung Chang, Worthington, Ohio

[73] Assignee: Ashland Oil, Inc., Ashland, Ky.

[21] Appl. No.: 600,437

[22] Filed: Apr. 16, 1984

Related U.S. Application Data

[63] Continuation-in-part of Ser. No. 414,565, Oct. 2, 1982, , and a continuation-in-part of Ser. No. 414,382, Oct. 2, 1982, , said Ser. No. 414,565, is a continuation-in-part of Ser. No. 332,558, Dec. 21, 1981.

[51] Int. Cl.$^4$ ............................................. C07C 45/50
[52] U.S. Cl. .................................. 568/454; 502/514; 568/909
[58] Field of Search ............... 502/514; 568/451, 454, 568/456, 909; 260/429 R

[56] References Cited

U.S. PATENT DOCUMENTS

| | | | |
|---|---|---|---|
| 3,463,741 | 8/1969 | Russell | 502/514 |
| 3,560,539 | 2/1971 | Booth | 568/456 |
| 3,755,393 | 8/1973 | Kniese et al. | 260/429 R |
| 3,806,538 | 4/1974 | Prognon et al. | 568/456 |
| 3,899,442 | 8/1975 | Friedrick | 568/456 |
| 4,013,583 | 3/1977 | Knifton | 502/514 |
| 4,013,584 | 3/1977 | Knifton | 502/514 |
| 4,113,754 | 9/1978 | Kummer et al. | 260/429 R |
| 4,135,911 | 1/1979 | Balmat | 568/456 |
| 4,306,086 | 12/1981 | Demay | 568/454 |
| 4,400,547 | 8/1983 | Dawes et al. | 568/454 |

FOREIGN PATENT DOCUMENTS

540957  1/1952  Canada .............................. 568/456

*Primary Examiner*—Werren B. Lone
*Attorney, Agent, or Firm*—Wood, Herron & Evans

[57] ABSTRACT

A method of reactivating anionic Group VIII hydroformylation catalysts to maintain high selectivity towards linear products. In the process of manufacturing aldehydes and alcohols from olefins, hydrogen, carbon monoxide and a catalyst, the selectivity for linear products is extremely high when an anionic Group VIII catalyst is used. This selectivity, after prolonged use of a catalyst, falls off along with the turnover number. The catalyst is reactivated to increase the selectivity towards linear products as well as the turnover number by subjecting the catalyst to a reducing agent which is strong enough under treatment conditions to reduce the anionic Group VIII catalyst. Reactivation of anionic iron, ruthenium, osmium, and mixed transition metal complex catalysts are particularly described and claimed.

16 Claims, No Drawings

METHOD OF REACTIVATING GROUP VIII ANIONIC HYDROFORMYLATION CATALYSTS

RELATED APPLICATION

This application is a continuation-in-part of application Ser. No. 414,565, filed Oct. 2, 1982, entitled Process For the Hydroformylation of Olefins to Produce Linear Aldehydes and Alcohols, which is a continuation-in-part of application Ser. No. 332,558, filed Dec. 21, 1981, entitled Process For the Hydroformylation of Olefins Using an Improved Ruthenium Catalyst and Improved Hydroformylation Catalyst. This application is also a continuation-in-part of application Ser. No. 414,382, filed Oct. 2, 1982, entitled Use of Mixed Metal Catalysts in The Hydroformylation of Olefins to Produce Linear Aldehydes and Alcohols.

BACKGROUND OF THE INVENTION

The present invention relates to a process for the hydroformylation of olefins to produce aldehydes and alcohols. The present invention more particularly relates to such a process in which anionic Group VIII and mixed transition metal complex catalysts are used which are extremely selective toward straight chain products. The present invention more particularly relates to the regeneration of these hydroformylation catalysts to maintain this high selectivity toward straight chain aldehydes and alcohols.

BACKGROUND OF THE INVENTION

Aldehydes and alcohols are extremely useful as general purpose solvents, as surfactants and as precursors to many other useful chemicals. Due to the extent to which these compounds are used, it is important that such compounds be biodegradable. It is known that linear aldehydes and alcohols are more easily biodegraded than branch-chain aldehydes and alcohols.

Further, certain straight chain aldehydes and alcohols are extremely useful in particular applications. One particular straight chain aldehyde which has particular utility is n-butyraldehyde. This aldehyde can be dehydrated to form 2-ethyl hexanol which is useful as a gasoline additive or the alcohol can be esterified with phthalic anhydride to produce dioctylphthalate which is used for plasticizing polyvinyl chloride resins.

One method of producing aldehydes and alcohols is the hydroformylation of olefins. Hydroformylation is an old reaction and is used commercially to prepare both straight and branch-chain aldehydes and alcohols. In this reaction, an olefin is reduced by the addition of carbon monoxide and hydrogen to form an aldehyde. This reaction can be carried further until the aldehyde is reduced to an alcohol. This is further explained in U.S. Pat. No. 3,876,672 which is incorporated herein by reference.

The hydroformylation reaction generally requires a catalyst. In the past, typical catalysts have included cobalt carbonyl, rhodium carbonyl, nickel, and platinum complexes. Although anionic metal catalysts are known, it has never been appreciated that the anionic character of the catalyst improves selectivity toward linear products. A problem encountered with the most commonly used prior art catalysts was the low percentage of linear aldehydes or alcohols produced. A reason for this is that the most commonly used catalysts were either cationic metal complexes or neutral or weakly anionic complexes.

In the co-pending application, particular anionic Group VIII metal catalysts have been disclosed which are very selective toward straight products. These include anionic ruthenium and iron compounds wherein the anionic moiety has at least a $-2$ charge as well as anionic osmium compounds and anionic mixed metal compounds.

SUMMARY OF THE INVENTION

The present invention involves the catalytic reaction or method in which aldehydes or alcohols are formed according to the following reaction:

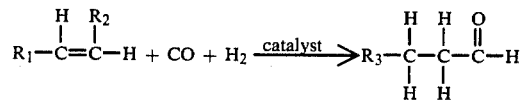

The reaction can be continued, reducing the aldehyde to linear alcohol. As the reaction continues, the catalyst tends to lose its selectivity. According to the present invention, the catalyst is reactivated, i.e., selectivity is improved by treating the catalyst with a reducing agent. The reducing agent must be strong enough to reduce the catalyst under treatment conditions.

DETAILED DESCRIPTION OF THE INVENTION

The hydroformylation reaction is an addition reaction in which carbon monoxide and hydrogen are reacted with an olefin to produce a saturated aldehyde. In other words, carbon monoxide and hydrogen are added to the olefin and the olefin reduced. The olefin can be reacted with carbon monoxide in the presence of hydrogen and a catalyst, or the olefin can be reacted with an excess of carbon monoxide and water in the presence of a catalyst. When carbon monoxide and water are used in the reaction, the water is simply a source of hydrogen, reacting with the carbon monoxide to form hydrogen and carbon dioxide. Hydrogen is thereby provided to react together with additional carbon monoxide upon the olefin. In either case, there is a hydrogen source available to react in combination with carbon monoxide upon the olefin. This reaction can be continued and available hydrogen would react with the aldehyde to produce an alcohol. The formation of the alcohol is encouraged by altering reaction conditions such as reaction time, pressure and temperature.

The hydroformylation reaction is shown by the following reaction formulas (I) and (II):

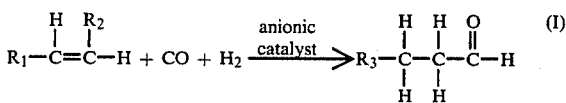

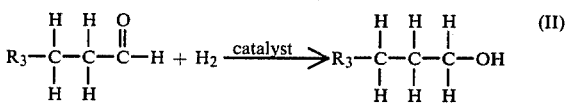

wherein $R_1$ represents alkyl, substituted alkyl, aryl or substituted aryl and $R_2$ represents hydrogen, alkyl, substituted alkyl, aryl or substituted aryl.

If $R_2$ is not hydrogen, the anionic catalyst used in the present invention will tend to cause the double bond in the olefin to migrate to form a linear aldehyde. $R_1$ or $R_2$ must, however, be either hydrogen or an unsubstituted alkyl group or the reaction will proceed at a very slow rate. $R_3$ will represent alkyl, substituted alkyl, aryl or substituted aryl and its formula will be determined by the make-up of $R_1$ and $R_2$. Thus, for example, if $R_1$ and $R_2$ are methyl groups, the hydroformylation will produce an aldehyde in which $R_3$ is an ethyl group. The double bond in the olefin will have migrated one carbon atom to form n-pentaldehyde.

The hydroformylation reaction is applicable to a wide variety of unsaturated compounds, including compounds containing more than one ethylenic group. Since difficulty has been experienced where the olefin is highly branched, two substituents of the olefinic group should be hydrogen as is shown in formula I. Hydroxyl or halogen substituents must be removed from the double bond by at least two carbon atoms and preferably not be present at all since they inactivate the catalyst in some situations.

Substituents which do not substantially interfere with the hydroformylation reaction include alkyl, aryl carbonyl, aryl $C_1$-$C_9$ alkoxycarbonyl, aralkyl, $C_1$-$C_9$ alkaryl, $C_1$-$C_9$ alkoxy and aryloxy. Aryl groups present may also be substituted by any of the other non-interfering substituents. The unsaturated compounds may contain up to 20 carbon atoms.

In order to obtain the full benefit of the present invention, $R_1$ and $R_2$ should be a straight chain $C_1$-$C_9$ alkyl group or $R_1$ or $R_2$ should be hydrogen. If $R_1$ and $R_2$ would be hydrogen, the product must necessarily be straight chain, i.e., propanal. Therefore, if ethylene is the olefin reactant, no benefit is derived from using the anionic catalysts of the present invention. When ethylene is the olefin reactant, a more reactive catalyst which is not necessarily selective toward linear products should be used.

The preferred olefin of the present invention should have the following general formula:

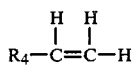
(III)

wherein $R_4$ is a straight chain $C_1$-$C_{18}$ alkyl. This olefin should react quickly with high selectivity toward linear product.

In the event a di-olefin were reacted to form a dialdehyde or dialcohol, the olefin should have the following general Formula IV.

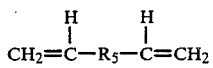
(IV)

wherein $R_5$ is an alkyl, substituted alkyl, aryl or substituted aryl, and preferably, a straight chain $C_1$-$C_9$ or higher alkyl.

Preferred olefins include: propylene, butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadecene-1, nonadecene-1, eicosene, 1,5-hexadiene, 1,6-heptadiene, 1,7-octadiene, 1,8-nonadiene, 1,9-decadiene, 1,10-undecadiene, and 1,11-dodecadiene.

CATALYSTS

The catalysts for use in the present invention are anionic Group VIII transition metal compounds. A general formula of one preferred anionic transition metal complex for use as hydroformylation catalysts in the present invention is:

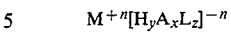

wherein A represents Fe, Ru and Os, M is a cationic species, n is an integer greater than or equal to 2 when A is Fe or Ru and n is an integer greater than or equal to 1 when A is Os; x is an integer greater than or equal to 1; y is an integer greater than or equal to 0, and z is an integer less than or equal to the available coordination bonding sites of the transition metal complex represented by $A_x$.

Typically, n will not exceed 6, y will not exceed 4 and is usually 2 or less, x will not exceed about 6. In theory, these upper limits may be exceeded, but known species generally fall within these limits. The ligands represented by L include any ligand whih will bond with the transition metal complexes and which will not interfere with the hydroformylation reaction. Ligands specifically suitable for use in the present invention include: trialkyl phosphines, trialkyl arsines, trialkyl antimonies, trialkyl bismuths, triaryl phosphines, triaryl arsines, triaryl antimonies, triaryl bismuths, carbon monoxide, cycloalkyldienes, isonitrile, isocyanide, acetylenes, crownethers, nitriles, such as phenyl nitrile, tertiary amines and halides. The choice of a ligand is critical in practicing the present invention. Those of ordinary skill in the art are well aware of many other suitable ligands.

M can represent any cationic species which will bond to the transition metal anionic complex and will not interfere with the hydroformylation reaction. Generally, M will be a metal and preferably selected from Group IA and Group IIA or an organic cation such as iminium, ammonium, phosphonium or arsenium. Again, one of ordinary skill in the art will be well aware of many other suitable cationic species. The above list is by no means meant to be exhaustive.

The hydroformylation catalysts may also be mixtures of transition metals wherein two transition metal compounds are combined in the reaction vessel. The first transition metal compound is a neutral or anionic transition metal compound selected from Group VIII of the Periodic Table. Preferably, these should be halides or carbonyls of the transition metals. Included are mono-, di- and multinuclear transition metal compounds as well as organotransition metal compounds.

Examples of these compounds would include $RhCl_3$, $RuCl_3$, $(Rh)(CO)_2Cl_2$, $Co_2(CO)_8$, $Rh_6(CO)_{16}$, $Ru_3(CO)_{12}$, $Ir_4(CO)_{12}$, $Os_3(CO)_{12}$, $Fe_3(CO)_{12}$, $Co_2Rh_2(CO)_{12}$, $HRh(CO)(PPh_3)_3$, $H_2Ru_4(CO)_{13}$, $H_2Ru_6(CO)_{18}$, $H_2PtCl_6$, $H_4Ru_4(CO)_{12}$, $PdCl_2(PPh_3)_2$, $HCoRu_3(CO)_{13}$, and so on. Preferably, the transition metal compound will be a halide or a carbonyl.

The second transition metal component of the catalyst of the present invention has the following general formula:

wherein B represents Fe, Ru, Os, W, Mo, Cr, Co, Rh and Ir;

M is a cationic species;

n is an integer greater than or equal to 2;

x is an integer greater than or equal to 1;

y is an integer greater than or equal to 0; and z is an integer less than or equal to the available coordination bonding sites of the transition metal complex represented by $B_x$. This catalyst is hereinafter referred to as the mixed metal catalyst.

Typically, n will not exceed 6, y will not exceed 4 and is usually 2 or less, x will not exceed about 36. In theory, these upper limits may be exceeded, but known species generally fall within these limits. The ligands represented by L include any ligand which will bond with the transition metal complexes and which will not interfere with the hydroformylation reaction. Ligands specifically suitable for use in the present invention include: trialkyl phosphines, trialkyl arsines, trialkyl antimonies, trialkyl bismuths, triaryl phosphines, triaryl arsines, triaryl antimonies, triaryl bismuths, tertiary amines, carbon monoxide, cycloalkyldienes, isonitrile, isocyanide, acetylenes, crownethers, nitriles, such as phenyl nitrile, and halides. This is by no means an exhaustive list. Those of ordinary skill in the art are well aware of different ligands which can be used in place of the ligands listed above.

M can represent any cationic species which will bond to the transition metal anionic complex and will not interfere with the hydroformylation reaction. Generally, M will represent one or more metals preferably selected from Group IA and Group IIA or an organic cation such as iminium, ammonium, phosphonium or arsenium. Again, this is not an exhaustive list of suitable cations. Those of ordinary skill in the art are well aware of different cations which can be used in place of those listed above.

HYDROFORMYLATION REACTION

The hydroformylation reaction is conducted by mixing the olefin, carbon monoxide, and a hydrogen source, i.e., hydrogen or water together with the catalyst, and optionally, a solvent in a continuous or batch-type reactor. Preferably, the solution is heated and maintained under increased pressure.

While the reaction will occur at room temperature, it is preferred to heat and maintain the solution at 120°–200° C. In general, if the temperature is decreased, the rate of the reaction decreases. But, as the temperature is increased above 200° C., the selectivity toward linear aldehydes and alcohols decreases. In addition, the increase in temperature increases the difficulty of controlling the reaction to obtain primarily aldehydes as opposed to alcohols should this be desired.

Preferably, for the production of straight chain aldehydes, the pressure of the reaction should be maintained at between 500 psi to 2500 psi. This combined with a mixing force causes the carbon monoxide to go into solution. The higher pressure also tends to increase both the reaction rate and the selectivity of the reaction toward linear products. However, increased pressure also promotes the continuation of the reaction to produce alcohols.

The reaction time will vary depending on the temperature and pressure. Generally, the reaction time is maintained between 0.5–10 hours. An increase in time will cause an increase in the production of alcohol. It should be noted that in order to obtain only linear aldehydes, the reaction time is kept to a minimum which in turn does not provide time for most of the olefin to react. This can be more fully appreciated by considering the examples provided below.

To increase the production of alcohol as opposed to the aldehyde, the reaction temperature should be above 160° C.; the pressure should be above 800 psi and the reaction time should be from 3–5 hours or longer. Analysis of the reaction products will enable one of ordinary skill in the art to select the preferred reaction conditions for a particular olefin and catalyst.

The reaction may be run with or without a solvent. Suitable solvents include aldehydes, alcohols, ethers, esters, ketones, nitriles, aromatic hydrocarbons, aliphatic hydrocarbons, and chlorocarbons. Particularly suitable solvents include tetrahydrofuran, dibutyl ether, diethyl ether, dioxane, 2-methoxyethyl ether, 1,2-dimethoxyethane, butyl alcohol, ethyl alcohol, ethylene glycol, isobutyl alcohol, n-butyraldehyde, ethyl acetate, amyl acetate, ethyl butyrate, methyl benzoate, acetone, methyl ethyl ketone, methyl isobutyl ketone, acetonitrile, propionitrile, benzonitrile, chloroform, ethylene dichloride, methylene chloride, chlorobenzene, the chlorotoluenes, benzene, toluene, xylene, hexane, heptane, octane, cyclohexane, and methylcyclohexane.

REACTIVATION OF THE CATALYST

After prolonged use of the catalyst, the selectivity towards linear products will tend to fall off. By monitoring the selectivity periodically, one can determine the point at which the reaction should be discontinued due to unsatisfactory selectivity towards linear products.

In order to reactivate the catalyst, the catalyst is treated with a reducing agent which under the reactivation or treatment conditions, is strong enough to reduce a neutral Group VIII metal. Reactivation conditions specifically refer to the temperature and pressure at which the catalyst is reactivated as well as the duration of the reactivation.

More specifically, in the reactivation procedure, the catalyst is removed from the reactor and placed in a separate container or flask. The solvent and aldehydes or alcohols present on the catalyst are removed by vacuum distillation. The catalyst residue is resolved in an anhydrous solvent, for example, 1,2-dimethoxymethane or tetrahydrofuran and treated with 1–15 molar equivalents of a reducing agent.

Suitable reducing agents would include alkali metal hydrides such as potassium hydride or sodium hydride, alkali metal benzaphenones, for example, potassium benzophenone, sodium benzophenone, alkali boron or aluminum hydrides, for example, potassium borohydride, and alkali metal naphthalene, for example, potassium naphthalene or sodium naphthalene.

The catalyst reducing agent mixture is then subjected to heat for a period of time. The temperature and duration of the reactivation procedure will depend upon the degree of deactivity (loss of selectivity) of the catalyst and strength of the reducing agent. A weaker reducing agent would require higher reactivation temperatures and/or a longer reactivation time. With the reducing agents listed above, the deactivation anionic Group VIII hydroformylation catalyst can be reactivated at a temperature from about 20° C. to about 150° C. in from about one minute to about 24 hours. Depending on the solvent systems used, the temperature may have to be maintained at less than about 100° C. or the reactivation may have to be conducted under elevated pressure conditions. Temperatures lower than 20° C., i.e., 0° C. or less may be used, but the reactivation would require more time than desirable. The 150° C. upper limit represents the approximate temperature at which the catalyst would revert to the neutral or metallic form. This temperature will vary depending on the particular catalyst. The reactivation should be conducted in a neutral atmosphere such as argon or nitrogen.

The resulting solution of catalyst can then be placed back into the reactor and once again used to produce linear aldehydes or alcohol.

These reactions can be further appreciated by reference to the examples provided below. Attention should be focused on the selectivity toward the linear product obtained. As can be seen by looking at these examples, the specificity toward a linear product is substantially improved after a deactivated catalyst has been reactivated using the method of the present invention. In each of these examples, the catalyst reactivated had been previously deactivated by using it to catalyze a hydroformylation reaction. The selectivity and turnover number of the deactivated catalyst is provided for each example.

EXAMPLE 1

A deactivated hydroformylation catalyst $(PNP)H_3Ru_4(CO)_{12}$ (83.9% selectivity toward linear product and turnover of 10.2) containing 0.20 mmol of ruthenium metal was placed in a flask. The solvent, aldehydes or alcohols produced during the hydroformylation reaction were removed by distillation under vacuum. The remaining catalyst residue was dissolved in 10 milliliters of anhydrous 1,2-dimethoxyethane and treated with 0.36 mmol of potassium tri-sec-butylborohydride. The reaction mixture was heated under argon at 60° C. for 24 hours.

Hydroformylation Reaction with Reactivated Catalyst

The resulting dark brown catalyst solution, 3 milliliters (19.1 mmol) of 1 octene and 70 milliliters of anhydrous 1,2-dimethoxyethane were placed in a 300 milliliter Hastelloy C autoclave. The reactor was sealed, flushed three times with carbon monoxide, pressurized with 860 psig of approximately equimolar mixture of carbon monoxide and hydrogen and heated to 180° C. with stirring. The pressure was maintained at 1,000 psig. The reaction proceeded for two hours. After the reactor cooled, the reaction products were drawn out and analyzed with gas chromatography. It was found that 23.7% of octene was converted into a mixture of n-nonanal (4.04 mmol, 95.7% selectivity) and branched aldehydes (0.18 mmol, 4.3% selectivity) with a total turnover of 17.7 mole of products produced to mole of ruthenium metal.

EXAMPLE 2

Partially deactivated $(PNP)_2Ru_6(CO)_{18}$ (83.9% selectivity with a turnover number of 10.2) hydroformylation catalyst solution containing 0.240 mmol of ruthenium metal was placed in a flask. Solvent, aldehydes or alcohols produced from the previous hydroformylation reaction were removed by distillation under vacuum. The catalyst residue left was reactivated by dissolving it in 10 milliliters of anhydrous 1,2-dimethoxyethane and treating the catalyst with 0.48 mmol of potassium-benzophenone. This reaction mixture was stirred under argon at room temperature for three hours.

Hydroformylation With Reactivated Catalysts

The resulting dark brown catalyst solution, together with 3 milliliters (19.1 mmol) of 1 octene, and 70 milliliters of anhydrous 1,2-dimethoxyethane were placed in a 300 milliliter Hastelloy C autoclave. The reactor was sealed, flushed three times with carbon monoxide, pressurized with 860 psig of approximately equimolar mixture of carbon monoxide and hydrogen and heated to 180° C. with stirring. The pressure was maintained at 1,000 psig. The reaction proceeded for two hours. The reactor was cooled and the reaction products drawn out and analyzed using gas chromatography. It was found that 31.4% of octene was converted into a mixture of n-nonanal (5.3 mmol, 94.1% selectivity) and branched aldehydes (0.33 mmol, 5.9% selectivity) with a total turnover number of 23.7 mole of product produced to mole of ruthenium metal.

EXAMPLE 3

A partially deactivated (PNP) $CoRu_3(CO)_{13}$ hydroformylation catalyst solution (58.2% selectivity and turnover of 4.3) containing 0.55 mmol of ruthenium metal and 0.18 mmol of cobalt was placed in a flask. The solvent and aldehydes or alcohols produced from the previous hydroformylation reaction were removed by distillation under vacuum. The catalyst residue left was dissolved in 10 milliliters of anhydrous 1,2-dimethoxyethane and treated with 1.1 mmol of potassium naphthalene. The reaction mixture was stirred under argon at room temperature for two hours.

Hydroformylation Reaction With Reactivated Catalyst

The resulting dark brown catalyst solution, 3 milliliters, (19.1 mmol) of 1 octene and 70 milliliters of anhydrous 1,2-dimethoxyethane were placed in a 300 milliliter Hastelloy C autoclave. The reactor was sealed, flushed three times with carbon monoxide, pressurized with 860 psig of approximately equimolar mixture of carbon monoxide and hydrogen and heated to 180° C. with stirring. The pressure was maintained at 1,000 psig. The reaction proceeded for three hours. The reactor was cooled and the reaction products drawn out and analyzed with gas chromatography. It was found that 44.2% of octene was converted into a mixture of n-nonanal (6.57 mmol, 96.4% selectivity) and branched aldehydes (0.25 mmol, 3.6% selectivity) with a total turnover number of 9.3 moles of products produced per mole of ruthenium metal.

EXAMPLE 4

A partially deactivated ruthenium carbonyl hydroformylation catalyst solution (84.1% selectivity, turnover 14) containing 0.270 moles of ruthenium metal was placed in a flask. The catalyst had been formed in situ by adding 3 equivalents of KH per mole of $Ru_3(CO)_{12}$ in the hydroformylation reaction vessel. Solvents and aldehydes or alcohols produced from the previous hydroformylation reaction were removed by distillation under vacuum. The catalyst residue left is dissolved in 10 milliliters of anhydrous 1,2-dimethoxyethane and treated with 0.49 mmol of potassium hydride. The reaction mixture was heated under argon at 65° C. for 24 hours.

Hydroformylation Reaction With Reactivated Catalyst

The resulting dark brown catalyst solution, 3 milliliters (19.1 mmol) of 1 octene and 70 milliliters of anhydrous 1,2-dimethoxyethane were placed in a 300 milliliter Hastelloy C autoclave. The reactor was sealed, flushed three times with carbon monoxide and hydrogen and heated to 180° C. with stirring while the pressure was maintained at 1,000 psig. The reaction was allowed to proceed for two hours. The reactor was then cooled, and products drawn out and analyzed with gas chromatography. It was determined that 38.2% of the octene was converted into a mixture of n-nonanal (6.56 mmol, 97.3% selectivity) and branched aldehydes (0.18 mmol, 2.7% selectivity) with a total turnover number of 25.0 moles of product produced per mole of ruthenium metal.

These examples demonstrate that the anionic hydroformylation catalysts, once deactivated can be reactivated by subjecting them to a strong reducing agent.

I claim:

1. The method of reactivating an anionic Group VIII hydroformylation catalyst wherein said catalyst has the following general formula:

$$M^{+n}[H_yA_xL_z]^{-n}$$

wherein
A represents a metal selected from the group consisting essentially of Fe, Ru and Os;
n represents an integer greater than or equal to 1;
M represents a cationic moiety;
y represents an integer greater than or equal to 0;
x represents an integer greater than or equal to 1;
L is a ligand; and
z is an integer less than or equal to the available coordination bonding sites of A;
said method comprising reducing said deactivated catalyst by contacting said catalyst with a reducing agent strong enough to reduce said hydroformylation catalyst.

2. The method of reactivating an anionic Group VIII hydroformylation catalyst claimed in claim 1 wherein said deactivated catalyst is contacted with said reducing agent by mixing said catalyst with said reducing agent in an organic solvent solution and heating said solution for a period of time effective to reactivate said catalyst.

3. The method of reactivating an anionic Group VIII hydroformylation catalyst as claimed in claim 2 wherein said catalyst and reducing agent are heated for about one minute to about 24 hours at from about 20° C. to about 150° C.

4. The method of reactivating an anionic Group VIII catalyst claimed in claim 3 wherein said reducing agent and said catalyst are heated for about one minute to about 24 hours at from about 20° C. to about 100° C.

5. A method of reactivating an anionic Group VIII hydroformylation catalyst as claimed in claim 3 wherein said reducing agent is selected from the group consisting of alkali metal hydrides, alkali metal benzophenones, alkali boron hydrides, alkali aluminum hydrides and alkali metal naphthalenes and mixtures thereof.

6. A method of reactivating an anionic Group VIII hydroformylation catalyst claimed in claim 5 wherein said reducing agent is selected from the group consisting of potassium hydride, sodium hydride, potassium benzophenone, sodium benzophenone, potassium borohydride, sodium borohydride, sodium aluminum hydride, potassium aluminum hydride, sodium naphthalene, potassium naphthalene and mixtures thereof.

7. The method claimed in claimed in claim 1 wherein A represents Os.

8. The method claimed in claim 1 wherein A represents Ru and n is greater than or equal to 2.

9. The method claimed in claim 1 wherein A represents Fe and n is greater than or equal to 2.

10. The method of reactivating an anionic Group VIII hydroformylation catalyst wherein said catalyst is a composition comprising in admixture a first transition metal compound and a second transition metal compound wherein said first transition metal compound is selected from the group consisting essentially of anionic and neutral Group VIII transition metal compounds; and wherein said second transition metal compound has the following general formula:

$$M^{+n}[H_yB_xL_z]^{-n}$$

wherein
n is an integer greater than or equal to 2; p1 M is a cationic species;
B is a transition metal selected from the group consisting essentially of Ru, Os, Fe, Cr, Co, Rh, Ir, Mo and W;
x is an integer greater than or equal to 1;
L is a ligand;
z is an integer greater than or equal to the available coordination bonding sites of B; and
y is an integer greater than or equal to 0;
said method comprising reducing said deactivated catalyst by contacting said catalyst with a reducing agent strong enough to reduce said catalyst.

11. The method claimed in claim 10 wherein said first transition metal compound is a carbonyl.

12. The method claimed in claim 10 wherein said first transition metal is a halide.

13. The method claimed in claim 10 wherein said first transition metal compound includes a transition metal selected from the group consisting of Rh, Os and Ru.

14. The method claimed in claim 10 wherein the molar ratio of the transition metals of the first transition metal compound to said second transition metal compound is from about 1:10 to about 1:1.

15. The method of reactivating an anionic Group VIII hydroformylation catalyst wherein said catalyst comprises:
a first transition metal compound wherein said transition metal is selected from the group consisting essentially of Fe, Ru, Os, Co, Rh, Ir, Ni, Pd and Pt, and wherein said first transition metal compound is a halide or a carbonyl compound;
a second transition metal compound having the following general formula:

$$M^{+n}[H_yB_xL_z]^{-n}$$

wherein
n is an integer greater than or equal to 2;
M is a cationic species;
B is a transition metal selected from the group consisting essentially of Ru, Os, Fe, Mo and W;
x is an integer greater than or equal to 1;
L is a ligand;
z is an integer less than or equal to the available coordination bonding sites of B; and
wherein the molar ratio of the transition metals of said first transition metal compound to said second transition metal compound is from about 1:1 to about 1:10 thereby providing an effective hydroformylation catalyst;
said method comprising contacting said catalyst with a reducing agent selected from the group consisting of alkali metal hydrides, alkali metal benzophenones, alkali boron hydrides, alkali aluminum hydrides and alkali metal naphthalenes and mixtures thereof at a temperature from about 20° C. to about 100° C. for about one minute to about 24 hours.

16. The method of reactivating an anionic Group VIII hydroformylation catalyst where said catalyst has been at least partially deactivated catalyzing the formation of linear alcohols and aldehydes from an olefin, carbon monoxide, and hydrogen source;

wherein said catalyst has the following general formula:

$$M^{+n}[H_yA_xL_z]^{-n}$$

wherein

A represents a metal selected from the group consisting essentially of Fe, Ru and Os;

n represents an integer greater than or equal to 1;

M represents a cationic moiety;

y represents an integer greater than or equal to 0;

x represents an integer greater than or equal to 1;

L is a ligand; and z is an integer less than or equal to the available coordination bonding sites of A;

said method comprising reducing said deactivated catalyst by contacting said catalyst with a reducing agent selected from the group consisting essentially of alkali metal hydrides, alkali metal benzophenones, alkali metal boron hydrides, alkali metal aluminum hydrides and alkali metal napthalenes and mixtures thereof at about 20° C. to about 150° C. for about one minute to about 24 hours.

* * * * *